United States Patent [19]

Ichihashi

[11] Patent Number: 4,832,043

[45] Date of Patent: May 23, 1989

[54] OPHTHALMIC DISEASE DETECTION APPARATUS

[75] Inventor: Tadashi Ichihashi, Hino, Japan

[73] Assignee: Kowa Company Ltd., Japan

[21] Appl. No.: 111,014

[22] Filed: Oct. 20, 1987

[30] Foreign Application Priority Data

Nov. 27, 1986 [JP] Japan .............................. 61-280777

[51] Int. Cl.$^4$ ............................................. A61B 13/00
[52] U.S. Cl. .................................. 128/745; 128/303.1; 351/221
[58] Field of Search ..................... 351/214, 221, 246; 128/303.1, 745, 665

[56] References Cited

U.S. PATENT DOCUMENTS

| 4,309,998 | 1/1982 | Rosa et al. ...................... | 128/303.1 |
| 4,702,576 | 10/1987 | Magnante ............................ | 351/214 |
| 4,711,542 | 12/1987 | Ichihashi et al. .................... | 351/221 |
| 4,743,107 | 5/1988 | Aizu et al. ........................... | 351/221 |

Primary Examiner—A. Michael Chambers
Attorney, Agent, or Firm—Bruce L. Adams; Van C. Wilks

[57] ABSTRACT

An apparatus for detecting ophthalmic diseases such as an inflammation in a patient's eye which includes a laser beam focussed at a selected spot in the eye. The light scattered from the eye is photoelectrically detected and converted into an electrical signal which is subsequently used to determine the protein concentration essential to ophthalmic disease detection in the patient's eye. The laser beam is deflected to scan the eye so far as to exceed a detection slit. The electrical signal derived when the laser beam is deflected outside the slit is used to remove noises from the electrical signal.

8 Claims, 3 Drawing Sheets

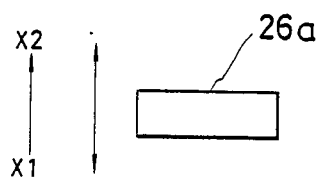
FIG. 3
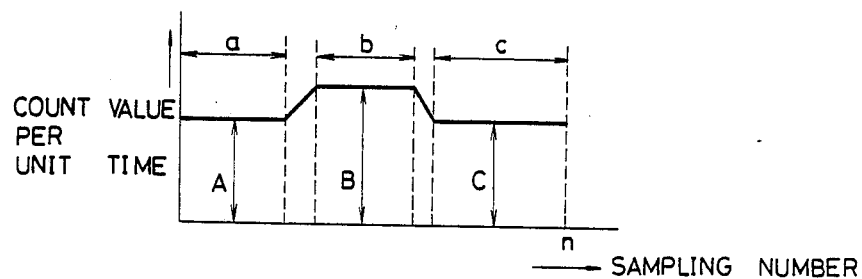
FIG. 4
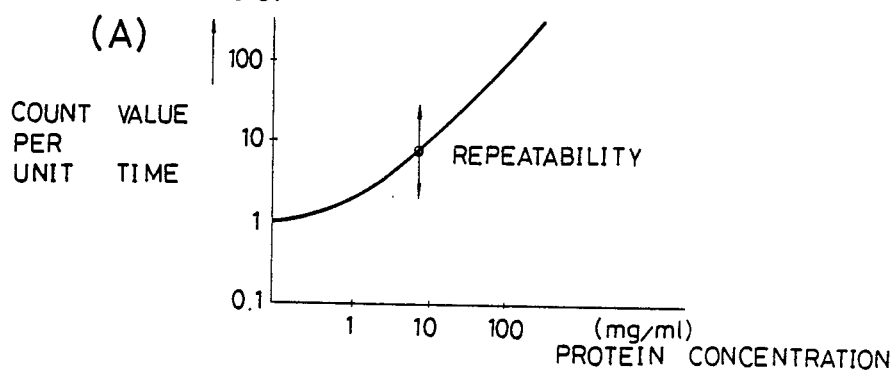
FIG. 5
(A)
(B)
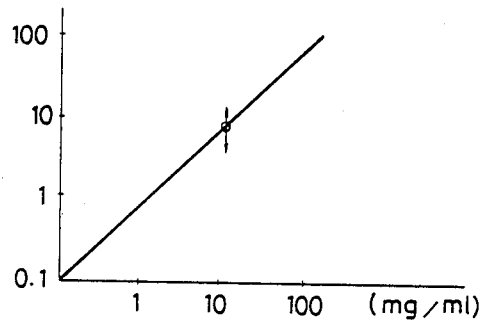

OPHTHALMIC DISEASE DETECTION APPARATUS

BACKGROUND OF THE INVENTION

1. Field of the Invention

This invention relates to an apparatus for detecting ophthalmic diseases in a patient's eye, and more particularly to an apparatus for detecting ophthalmic diseases in which laser light is radiated via an optical system at one spot in the camera oculi of the patient's eye, particularly in the anterior chamber thereof and the laser light scattered therefrom is analyzed to measure the protein concentration for ophthalmic disease detection in the camera oculi.

2. Description of the Prior Art

The camera oculi is comprised of the camera oculi anterior (anterior chamber) and the camera oculi posterior (posterior chamber). The camera oculi anterior is defined by a space surrounded by the rear surface of the cornea, a part of ciliary body, iris, and the front surface of the crystalline lens, while the camera oculi posterior is defined by a space surrounded by the rear surface of the iris, inner surface of the ciliary body, and front surface of the crystalline lens. The camera oculi is filled with transparent humor aqueous, which has chemical and physical characteristics different from lymphatic liquid and has a close relation with the metabolism of the cornea or crystalline lens. The humor aqueous contains proteins which increase causing the camera oculi to be turbid when it becomes inflamed.

In this respect, the measurement of protein concentration in the camera oculi of the patient's eye is of great importance in determining whether the camera oculi is inflamed., that is, whether a blood-aqueous barrier exists or not.

To measure the protein concentration in the camera oculi, a slit lamp microscope is very often used to determine the turbidity by grading via naked eyes. This is, however, disadvantageous because the judgment depends upon the person who performs the measurement.

On the other hand, a photographic measuring method has been developed to make a quantitative measurement of the protein concentration. This method is, however, too complicated to analyze, thus very difficult to apply in a clinical examination.

To overcome this problem, an apparatus for detecting the ophthalmic diseases has been proposed which includes means for focussing a laser beam at a selected spot in the camera oculi of an eye. In the apparatus, the light scattered from the eye is photoelectrically detected and converted into an electrical signal which is subsequently used to determine the protein concentration essential to ophthalmic disease detection in the camera oculi of the patient's eye. See, for example, Japanese Patent Laying-open No. 120834/87.

This apparatus, however, has also the drawback that the light reflected or scattered at the cornea, iris, lens or artificial lens after the cataractous operation impinges on the spot to be measured in the anterior chamber or intrudes into the laser scattered light in the form of noises. This disadvantageously makes the measurement inaccurate and the measured value poorly repeatable.

SUMMARY OF THE INVENTION

It is therefore an object of the present invention to provide an apparatus for detecting ophthalmic diseases which is capable of easily and precisely measuring the protein concentration in a patient's eye.

It is another object of the present invention to provide an apparatus for detecting ophthalmic diseases which is capable of reducing or removing noise due to the reflected or scattered light which may impinges on the spot be measured in the patient's eye.

In accordance with the present invention, the ophthalmic disease detection apparatus disclosed herein includes means for focussing a laser beam at a selected spot in a patient's eye. The laser beam is deflected in a predetermined direction to scan an area including the spot to be measured in the patient's eye. The apparatus further includes photoelectric converting means for receiving light scattered from the patient'eye and converting it into an electric signal, and a mask disposed in the front of the photoelectric converting means and formed thereon with a slit having a predetermined width to limit the impinging of the scattered light on the photoelectric converting means. The laser beam is deflected so far as to exceed the slit width. Further there is provided means for processing a first electric signal derived from the photoelectric converting means when the laser beam is deflected inside the slit width and a second electric signal derived therefrom when the laser beam is deflected outside the slit width. The second electric signal is used to remove or reduce a noise component from the first electric signal.

Thus, such an arrangement according to the present invention makes it possible to remove noise based on the dark current in the photoelectric converting means or unnecessary scattered or reflected light contained in the electrical signal from the photoelectric converting means, thus providing powerful and effective means for ophthalmic disease detection, particularly for the detection of inflammation in the camera oculi of the eye.

In a preferred embodiment of the present invention, an average of the second electric signal is subtracted from an average of the first electric signal to derive a significant signal component from the first electric signal.

In a preferred embodiment, the processing means comprises a counter for counting the number of pulses generated when the intensity of the scattered light received by the photoelectric converting means exceeds a predetermined level, a memory for storing the count value from the counter, and means for processing data in the memory to calculate the protein concentration on the selected spot in the patient's eye.

BRIEF DESCRIPTION OF THE DRAWINGS

The object and features of the present invention will become more apparent from a consideration of the following detailed description taken in conjunction with the accompanying drawings in which:

FIG. 3 is an illustrative view showing the scope of deflection of a laser beam;

FIG. 4 is a waveform derived from the scanning deflection of the laser beam; and FIGS. 5A and 5B are a diagram showing the relation between the count value and protein concentration according to the prior art and the present invention, respectively.

DETAILED DESCRIPTION OF THE PREFERRED EMBODIMENTS

Figure 1:
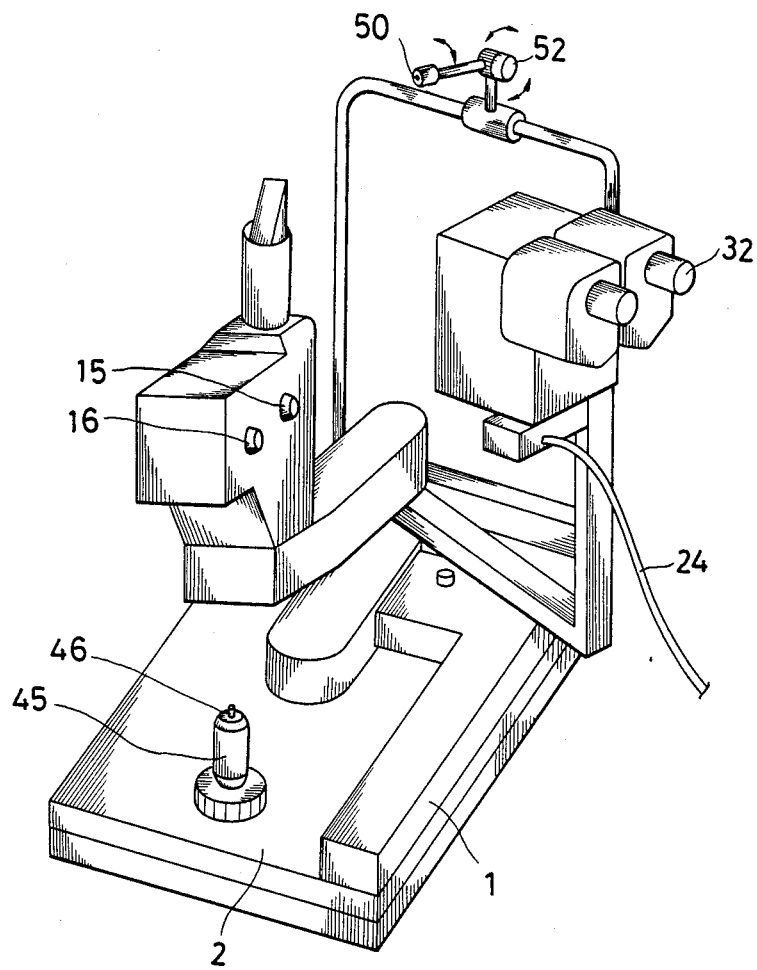
FIG. 1 is a schematic perspective view showing the whole appearance of the apparatus of the present invention.
Figure 2:
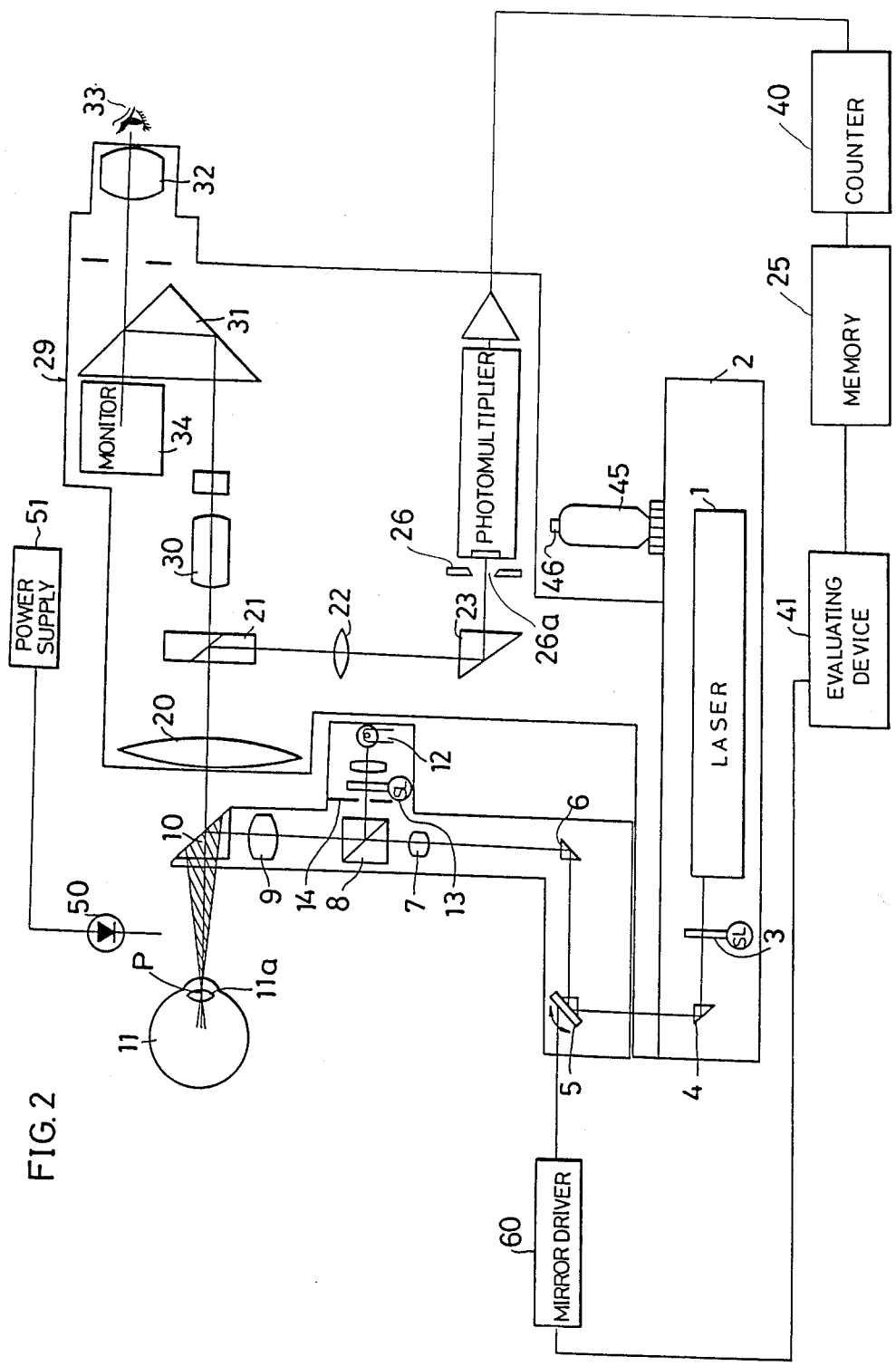
FIG. 2 is a block diagram showing the optical arrangement of the apparatus.

FIG. 1 and FIG. 2 show the general arrangement of an ophthalmic disease detection apparatus according to the present invention. In the drawings, reference numeral 1 indicates a helium-neon or argon type laser light source. The laser light source 1 is provided on a base 2. The light emitted from the laser light source 1 is passed through a laser filter 3, a prism 4, a swingable mirror 5, a prism 6, a lens 7, a beam splitter 8, a lens 9 and a prism 10, and converged at one spot in a camera oculi 11a of a patient's eye 11.

A slit light source 12 is provided in the laser emitting portion, and the light emitted from this slit light source 12 passes through a slit light shutter 13, a slit 14, and via the beam splitter 8, the lens 9 and the prism 10, whereupon it is imaged as a slit image on the camera oculi 11a or anterior chamber. Because the light emitted from the above mentioned laser light source 1 is converged as a spot of light, the slit light image is intended to illuminate the periphery of the light spot and thereby make the verification of the location of the spot image easy.

Adjustment as well as switching of the length of the slit along the lengthwise dimension of the slit 14 are carried out by means of an adjusting knob 15 and a switching knob 16, respectively.

Part of the laser light scattered from the spot being measured in the camera oculi 11a passes through the objective lens 20 of a detector 29, and is then divided by a beam splitter 21, whereupon a portion of the light passes through a lens 22, a prism 23, an optical fiber 24, a lens 35, and a shutter 36, and strikes a photomultiplier 27 which performs the function of a photoelectric converter. A mask 26 with a slit 26a having a certain width is disposed in the front of the photomultiplier 27, to limit the impinging of the scattered light thereon. Another portion of the scattered light divided by the beam splitter 21 is directed in another direction and passes through a variator lens 30, a prism 31, and a monitoring plate 34. The image may be observed by an examiner 33 through an eyepiece 32.

The output signal of the photomultiplier 27 is amplified by an amplifier 28 and then applied to a counter 40 for counting the number of photons, thus determining the intensity of the scattered light detected by the photomultiplier 27. The counter 40 counts the number of pulses appearing. When the photomultiplier 27 receives the scattered light greater in intensity than a predetermined value, the counter 40 produces an output signal, which is stored in memory 25 and is then applied to an evaluating device 41 to calculate the protein concentration in the camera oculi 11a.

The swingable mirror 5 is swung by mirror driver 60 connected to the evaluating device 41 to deflect the laser beam and move the laser spot in the anterior chamber for scanning. The scanning movement of the laser spot is performed around the center of the slit 26a in the longitudinal direction exceeding the width of the slit 26a.

In the present invention, an eye fixation lamp 50 comprising a light emitting diode fed by a power supply 51 is disposed in such a position as to enable the patient to fix the gaze of his eye thereto. The shade of light emitted by the eye fixation lamp 50 is selected so as to differ from the shade of light emitted by the laser light source 1. As an example, if the light emitted from the laser light source is red, the light emitted by the eye fixation lamp may be green. This eye fixation lamp 50 may be swiveled in the directions indicated by the arrows according to a linkage 52, and hence is adjustable to the optimal position for any given patient.

An input device such as, for example, a joy stick 45 equipped with a push-button 46 is provided on the base 2, the manipulating of which effectuates the insertion of the laser filter 3, the slit light shutter 13, and the shutter 36 into the optical system, as well as the extraction of same therefrom.

The operation of an apparatus with such an arrangement will be explained below. Immediately preceding measurement, the light source 12 is turned on, and the slit image of the slit 14 is passed through the beam splitter 8, the prism 10 and the lens 9 and imaged on the camera oculi 11a over an area that covers the spot P to be measured. Next, light from the laser light source 1 is passed through the optical arrangement of same and caused to converge on the spot P to be measured.

The laser light beam is then scattered from the spot P, whereupon the beam splitter 21 directs a portion of the scattered light in the direction of the examiner 33 for observation, and simultaneously sends another portion thereof to the photomultiplier 27 via the optical system comprising the lens 22, the prism 23, and the optical fiber 24.

On the other hand, the mirror 5 is caused to swing by the mirror driver 60 as shown by the arrows to thereby deflect the laser beam and scan the camera oculi longitudinally about the spot P to be measured. The scanning width or scope is set in the range of X1 to X2 as shown in FIG. 3. Accordingly, the width of the slit 26a on the mask 26 disposed in the front of the photomultiplier 27 is made smaller than the scanning scope by the laser beam. The photomultiplier 27 receives the scattered laser light through the slit 26a and detects the intensity of the light scattered by the protein particles in the camera oculi 11a of the patient'eye. The intensity of the scattered light is then converted to a train of pulses which are counted by the counter 41 in terms of the number of pulses per unit time. The count value is stored in the memory 25 including a plurality of locations each serving to store the number of counted pulses per unit time.

FIG. 4 shows the count value per unit time stored in the memory 25, which will be obtained when the laser spot is deflected from the positions X1 to X2 as shown in FIG. 3.

In FIG. 4, sections a and c represent portions when the laser beam doesn't impinge on the slit 26a. The signal in these sections primarily contains noise components due to the light reflected or scattered in the patient'eye. Assume that A and C indicate the average of the count value in the memory in the sections a and c. It is to be noted that the signal levels A and C also contain noise due to the dark current in the photomultiplier 27. These noise components fluctuate for each measurement, thus making the measurement inaccurate and unstable.

The section b, on the other hand, indicates a section in which the scattered laser beam impinges on the photomultiplier 27 through the slit 26a. The signal in this section contains the signal component corresponding to the protein concentration in the anterior chamber and the noise components based on the reflection and or scattering in the patient's eye and on the dark current in the photomultiplier. The symbol B indicates the average count value in the memory 25 in this section b.

The evaluating device 41 subtracts the values A or C from the value B to derive therefrom the significant signal component and calculate the protein concentration in the camera oculi.

In the prior art, the measurement was made only in the section b. This made the ratio S/N poor, causing a big fluctuation with bad repeatability in data processing (see FIG. 5A). The apparatus according to the present invention, on the other hand, improves the ratio SN and the dynamic range and provides an improved repeatability in data processing as shown in FIG. 5B because the noise component can be removed.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

I claim:

1. An apparatus for detecting ophthalmic diseases in a patient's eye comprising:
    a laser source for producing a laser beam;
    means for focussing said laser beam at a selected spot in said patient's eye;
    means for deflecting said laser beam in a predetermined direction to scan an area including said spot in the patient's eye;
    photoelectric converting means for receiving light scattered from said patient's eye and converting it into an electric signal;
    a mask disposed in the front of said photoelectric converting means and formed with a slit having a predetermined width configured to limit the impinging of the scattered light on said photoelectric converting means when said laser beam is deflected to exceed the slit width; and
    means for processing a first electric signal derived from said photoelectric converting means when said laser beam is deflected inside the slit width and a second electric signal derived therefrom when said laser beam is deflected outside the slit width to remove a noise component from said first electric signal with the second electric signal.

2. An apparatus as set forth in claim 1, wherein the processing means includes means for subtracting an average of said second electric signal from an average of said first electric signal to derive a significant signal component from said first electric signal.

3. An apparatus as set forth in claim 1, wherein said processing means comprises a counter for counting number of pulses generated when the intensity of the scattered light received by said photoelectric converting means exceeds a predetermined level, a memory for storing the count value from said counter, and means for processing data in said memory to calculate the protein concentration on said selected spot in the patient's eye.

4. An apparatus as set forth in claim 1, wherein said selected spot lies in the camera oculi anterior in the patient's eye.

5. An apparatus for detecting ophthalmic disease, comprising:
    means for producing a laser beam;
    means for focussing the laser beam at a selected spot in a patient's eye and including means for deflecting the beam to scan an area including said spot;
    means for converting light into an electrical signal;
    means receptive of light scattered from a patient's eye for applying same to the converting means and including masking means for blocking the application of scattered light to the converting means at only at least one portion of the area scanned by the deflected beam, whereby during a scan the converting means produces a first electrical signal when the scattered light is not blocked and a second electrical signal when the light is blocked; and
    signal processing means receptive of the first and second electrical signals for using the second electrical signal to remove noise components from the first electrical signal.

6. The apparatus according to claim 5, wherein the masking means comprises a mask having a slit with a slit width configured to permit passage of scattered light from one portion of the scanned area.

7. The apparatus according to claim 5, wherein the signal processing means comprises means for computing an average value of said first and second electrical signals and subtracting the average value of the second signal from that of the first electrical signal.

8. The apparatus according to claim 5, wherein the signal processing means comprises a counter for counting the electrical signals from the converting means when the intensity of scattered light is greater than a predetermined level, a memory for storing the count in the counter and means for processing data from the memory to calculate protein concentration at said selected spot.

* * * * *